United States Patent [19]

King

[11] Patent Number: 5,108,610
[45] Date of Patent: Apr. 28, 1992

[54] METHOD FOR ISOLATING DITHIOCHROME, AN INSULIN-BINDING MOLECULE WITH GLUCOSE METABOLISM-RELATED PHARMACEUTICAL UTILITY

[75] Inventor: Scott King, San Francisco, Calif.

[73] Assignee: Thymax Corporation, San Francisco, Calif.

[21] Appl. No.: 713,078

[22] Filed: Jun. 11, 1991

Related U.S. Application Data

[62] Division of Ser. No. 409,546, Sep. 19, 1989.

[51] Int. Cl.$^5$ .............................................. B01D 15/08
[52] U.S. Cl. .................... 210/635; 530/304; 530/305; 530/413; 530/417; 514/866; 514/504; 425/655; 424/655
[58] Field of Search ............... 530/413, 417, 303, 304, 530/305; 210/635, 656; 514/783, 866, 505; 424/655, 195.1; 436/161

[56] References Cited

U.S. PATENT DOCUMENTS 4,985,439  1/1991  Hwang et al. ...................... 514/312

OTHER PUBLICATIONS

"Preparation of Chromium-Containing Material of Glucose Tolerance Factor Activity from Brewer's Yeast Extracts and by Synthesis", J. Agric. Food Chem., vol. 25, No. 1, pp. 162–166, Toepfer et al., 1977.
"Present Knowledge of the Role of Chromium", Federation Proceedings, vol. 33, No. 11, pp. 2275–2280, Mertz et al., Nov. 1974.

*Primary Examiner*—Stanley S. Silverman
*Assistant Examiner*—Neil M. McCarthy
*Attorney, Agent, or Firm*—Oblon, Spivak, McClelland, Maier & Neustadt

[57] ABSTRACT

A process for obtaining a material possessing glucose tolerance factor activity and capable of binding with insulin including the steps of (i) contacting a eukaryotic cell mass with a mixture of water and alcohol to form a water phase and an alcohol phase; (ii) separating the alcohol phase from the water phase and isolating a water phase extract; and (iii) subjecting the water phase extract to gel exclusion chromatography, eluting all material having a molecular weight of approximately 720 to 1120 to obtain a material possessing glucose tolerance factor activity and capable of binding with insulin.

3 Claims, 10 Drawing Sheets

METHOD FOR ISOLATING DITHIOCHROME, AN INSULIN-BINDING MOLECULE WITH GLUCOSE METABOLISM-RELATED PHARMACEUTICAL UTILITY

This is a division of application Ser. No. 07/409,546, filed on Sept. 19, 1989.

BACKGROUND OF THE INVENTION

1. Field of the Invention

The present invention relates to processes for the extraction of a highly pure material heretofore available in low purity levels and known as glucose tolerance factor (GTF).

2. Discussion of the Background

The importance of dietary chromium and its function in biological systems is long-established. Chromium is an essential trace metal which has been suggested to have an importance role in normal glucose homeostasis. Deficiency of chromium, or of its biologically active form, has been implicated in the pathogenesis of some forms of glucose intolerance and diabetes mellitus.

Beginning in 1957, various investigators have sought to purify from natural sources, or synthesize, a chromium-containing material called GTF, believed to be the biologically active form of chromium. At best only partially purified materials (5 to 10% wt. pure as measured by analysis of sample chromium content) were obtained from natural sources. Synthetic efforts failed to yield GTF.

GTF is reported to be a naturally occurring low molecular weight (600–1000 dalton) organic compound which is water soluble and stable against wet heat, acid, and alkyl treatments. Various investigators have reported that GTF is a complex of nicotinic acid, amino acid components, and $Cr^{+3}$ Glycine, cysteine, and glutamic acid have been reported as appearing to be the amino acid components. See, Mooradian et al, Am. J. Clin. Nutr., (1987), 45:877-895. Chem., (1977)

Toepfer et al, J. Agric. Food Chem., (1977) 25(1):162–166 report that when Brewer's yeast is extracted with dilute alcohol and purified by ion exchange chromatography a product is obtained which possesses GTF activity. This material is reported to contain chromium, nicotinic acid, glycine, glutamic acid, and cysteine.

Toepfer et al also report that when 1 equivalent of trivalent chromium, $Cr(Ac)_3 \cdot H_2O$, is reacted with 2 equivalents of nicotinic acid, 2 equivalents of glycine, 1 equivalent of glutamic acid and 1 equivalent of cysteine a mixture of chromium complexes exhibiting GTF properties are obtained. These materials are however reported to be unstable, precipitating near neutral pH with resulting loss of biological activity.

Although various attempts have been made to isolate a purified form of the GTF product from natural sources and various attempts have been made to produce this material using synthetic methods, obtaining a purified GTF product has so far eluded investigators. In light of the importance of dietary chromium and problems associated with chromium deficiency, such as, e.g., insulin resistant diabetes, there is a strongly felt need for a method for readily obtaining a purified GTF, or a material possessing the biological activity of GTF, in substantial quantities.

SUMMARY OF THE INVENTION

Accordingly, it is an object of this invention to provide a method for efficiently obtaining a purified material having a high level of glucose tolerance factor activity.

The inventors have now discovered a process which satisfies all of the above objects of this invention and other objects which will become apparent from the description of the invention given hereinbelow.

The product obtained by using the process of the present invention is a compound named dithiochrome (DTC) by one of the inventors and which possesses a very high level of glucose tolerance factor activity.

In accordance with the present process, dithiochrome is readily obtained by subjecting a eukaryotic cell mass, wherein the eukaryotic cell mass is either a yeast cell mass or a ground cell mass of animal or plant origin, to dissolution in a water/alcohol mixture to obtain a water extract. This is followed by subjecting the water phase extract to centrifugation and sulfhydryl exchange chromatography. Dithiochrome binds to the sulfhydryl exchange column. After washing the column, the dithiochrome may be obtained by treating (eluting) the column with a low concentration of a reducing agent, e.g., an active thiol or dithiol.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

The present invention makes possible the efficient and facile production, from natural sources, of a highly pure material containing glucose tolerance factor activity, a compound that is an essential part of normal glucose metabolism and which has been named dithiochrome by the inventor.

Because it was believed that GTF was present in yeast and other materials in low concentrations and because of its perceived relative instability, it had heretofore been believed that it would be especially difficult to obtain a sufficient amount of this product from natural materials to permit elucidation of its structure. The present invention is in part due to the inventors' discovery of a facile process which readily yields substantial amounts of this material, renamed DTC, in highly purified form.

Dithiochrome may be found in all eukaryotic cells, including yeast and both cells of animal and plant origin. It is found however in large amounts in yeast, liver, kidney, mushrooms and black pepper. Because of its high concentration in yeast and the low cost of this material, yeast is a preferred source for dithiochrome.

In one embodiment of this invention, dithiochrome is obtained by:

(i) contacting a eukaryotic cell mass with a mixture of water and an alcohol, wherein said eukaryotic cell mass is either a yeast cell mass or a ground cell mass of animal or plant origin;

(ii) separating the alcohol phase from the water phase and obtaining a water phase extract, that is optionally freeze-dried;

(iii) applying the water phase extract to sulfhydryl exchange chromatography matrix;

(iv) washing the chromatography matrix; and (v) treating the chromatography matrix with an active thiol or dithiol to obtain a material capable of binding with insulin.

In a preferred embodiment of this invention, dithiochrome is obtained from yeast by:

(i) contacting yeast flakes, such as Brewer yeast (*Saccharomyces cerevisiae*, e.g., *Saccharomyces carlsbergensis*) flakes with a mixture of water and an alcohol;

(ii) separating the alcohol phase from the water phase and obtaining a water extract;

(iii) contacting the water phase extract with a sulfhydryl exchange chromatography matrix;

(iv) washing the chromatography matrix; and (v) eluting dithiochrome from the chromatography matrix using an active thiol to obtain a purified product.

In another embodiment, the inventor has discovered that an extract containing at least 35% wt. dithiochrome may be obtained by subjecting the water extract obtained in step (ii) above to gel exclusion chromatography and eluting all material having a molecular weight of approximately 920 (i.e. 720 to 1120, preferably 820 to 1020). For example, 6 grams of the freeze-dried water extract may be reconstituted in 5 ml of water. The solution obtained is then subjected to gel exclusion chromatography using, eg., a Sephadex G-25 column. By collecting all of the material having a molecular weight approximately 920 (i.e. 720 to 1120, preferably 820 to 1020) and concentrating, one obtains a product containing at least 15% wt., and generally at least 40% wt., of DTC. (The content of DTC being determined on the basis of a UV analysis of the sample at $\lambda = 262$ um and calculating the amount of DTC present as a function of the amount of nicotinic acid found.)

As noted above, the eukaryotic cell mass used may be of animal origin or plant origin. With eukaryotic cell of animal or plant origin, and in particular with cells of plant origin, it is advantageous to grind the cell mass or subject the cell mass to shear forces, e.g., this cell mass is ground or treated with a blender, prior to contacting the cell mass with the mixture of water and alcohol.

The cell mass is then dissolved in a mixture of water and alcohol. The alcohol is used in an amount effective to denature proteins and disrupt the cells of the mass, i.e., in an amount of 1 to 99% (v/v), preferably 25 to 50% (v/v), with the water.

Any lower alcohol which is miscible with water may be used, and combinations of these alcohols may also be used. These alcohols may contain from 1 to 5 carbon atoms, and may be linear, cyclic or branched. Illustrative examples of these alcohols include methanol, ethanol, n-propanol, i-propanol, n-butanol, i-butanol, t-butanol, n-pentanol, etc.

The requirement imposed on the alcohol phase used is that, at 22° C., it forms two separate phases with water. Some of the alcohols which may be used, e.g. methanol and ethanol, do not satisfy this condition. Such alcohols are accordingly used with a higher molecular weight alcohol in an amount appropriate to obtain an alcohol phase which forms two phases with water at 22° C.

The eukaryotic cell mass is homogenized in this water/alcohol mixture for from ½ hour, preferably 2 hours to 24 hours, or longer, if necessary. The alcohol phase and the water phase are then allowed to form and are separated, preferably by centrifugation.

The alcohol phase is discarded and the water phase is subjected to filtration to cause the elimination of material not dissolved in the aqueous phase.

The precipitate obtained from the water phase is discarded and the water phase is then subjected to lyophilization (or any other known method for concentrating an aqueous biological extract which does not inactivate DTC, for example, reverse osmosis or ion exchange chromatography) to obtain a water extract. The water extract is then subjected to sulfhydryl exchange chromatography.

The sulfhydryl exchange chromatography column used in the present invention may be any sulfhydryl exchange chromatography substance supported on, e.g., a polysaccharide, agarose, cellulose, dextran, any other inert polymeric support or a silicon support, e.g., Actigel T ™ (available from Sterogene, 140 E. Santa Clara Street, Arcadia, Cal., USA, 91006) or, e.g., sulfhydryl exchange material available on agarose from Pharmacia, Bio-Rad and Sigma Chemical Co. of St. Louis, Mis. 63178 USA, called Activated Thiol-Sepharose ™ or Affigel 501 ™.

Once the water phase extract has been subjected to the chromatography matrix, the chromatography matrix is then subjected to a washing step to obtain a steady base line. In this washing operation any solution with moderate ionic strength may be used with care being taken to avoid ions known as ligands of $Cr^{+3}$, i.e. chloride ions. In this washing operation, for example, a 25 mM potassium phosphate buffer (pH =7.2) may be used.

Once a steady base line is obtained, the chromatography matrix is eluted with a reducing agent, e.g., a gradient of active thiol or dithiol. The gradient of active thiol or dithiol is performed at a dithiol concentration going from 0 mM to 20 mM or at a thiol concentration of from 0 mM to 40 mM. Elution of dithiochrome begins at approximately 7 mM of active dithiol (DTE) or 14 mM of active thiol, at room temperature. Alternatively, DTC may be eluted by using a dithiol solution having a concentration of at least 7 mM (and up to 20 mM) or a thiol solution having a concentration of at least 14 mM (and up to 0.5 M).

The active thiol or dithiol which may be used to elute the dithiochrome may be any low molecular weight, water soluble, thiol or dithiol containing at least one sulfhydryl group. These include materials containing from 2-6 carbon atoms. These active thiols may contain additional hydroxyl groups to improve their water solubility. Exemplary thiols/dithiols include dithiothreitol (DTT), dithioerythritol (DTE), glutathione, thioglycerol, 2-mercaptoethanol, lipoic acid, and cysteine.

The purification procedure may be carried out at any practical temperature. Thus, for example, a temperature of from $-10°$ C. to $35°$ C., preferably $10°$ C. to $35°$ C., and more preferably $20°$ C. to $30°$ C., may be used.

The compound obtained by this process provides a positive Ninhydrin test for primary and secondary amines, with a ratio of secondary to primary means of about 2.7:1. It has a peak in the UV spectrum at 262 nm (nicotinic acid), and elutes from a DEAE column at 0.5 M NaCl.

Dithiochrome binds with insulin when the two materials are combined in the same solution. This provides an insulin-dithiochrome adduct. Dithiochrome and the adduct may be administered using any method for the administration of a pharmaceutically active material; that is enteral, suppository, subcutaneous, intravenous, intramuscular and transdermal methods may be used.

For example, dithiochrome may be administered to diabetics to alleviate their diabetes, where it may be administered in two forms. Dithiochrome may be given orally for the treatment of type II diabetes, insulin resistant diabetes, gestational diabetes, stress induced diabetes, obesity, hyperlipidemia, and other conditions associated with elevated blood glucose or suboptimal glucose kinetics. The insulin-dithiochrome adduct ("activated insulin"), may be used to treat a patient, in a manner similar to conventional insulin injection, as a therapy for type I (juvenile or insulin-dependent) diabetes.

For example, the insulin-dithiochrome adduct may be obtained by adding insulin and dithiochrome to a solution of 25 mM potassium phosphate (KP) buffer (pH=7.2) and allowing the solution to stand overnight at a temperature of $4°$ C. The insulin-dithiochrome adduct may be recovered from the solution by subjecting the solution to size exclusion chromatography.

Salts of dithiochrome and of the insulin-dithiochrome adduct, and in particular physiologically acceptable salts of the materials, are within the scope of this invention. Such salts contain a physiologically acceptable cation for example the cation of an alkali metal such as sodium, quaternary ammonium ions or protonated amines. Salts may be advantageously used because they impart greater water solubility.

Dithiochrome and the insulin-dithiochrome adduct may be formulated for use as pharmaceuticals for veterinary, for example in a mammalian context, or particularly human use by a variety of methods. Thus the present invention further provides pharmaceutical compositions containing either dithiochrome or an insulin-dithiochrome adduct, present each in an amount of 1 to 99 wt.%, each together with a physiologically acceptable carrier or diluent.

The insulin-dithiochrome adduct may be administered to a patient as an aqueous, oily or emulsified composition incorporating a liquid diluent which is usually employed for parenteral (both intravenous and intramuscular injections are possible) administration and is therefore sterile and pyrogen free.

Dithiochrome may be administered orally. For oral administration, compositions incorporating a liquid diluent containing dithiochrome may be used. For example, a conventional solid carrier material such as starch, lactose, dextrin or magnesium stereate may be used which permits the oral composition to be provided in a formed shape, for example as tablets, capsules (including spansules), etc.

Other forms of administration than by injection or through the oral route are possible in both human and veterinary contexts for both dithiochrome and the insulin-dithiochrome adduct. For example other forms known in the art such as the use of suppositories or pessaries may be used, particularly for human administration.

Pharmaceutical compositions may be formulated in unit dosage form, i.e., in the form of discrete portions each comprising a unit dose, or a multiple or sub-multiple of a unit dose. While the dosage of active compound (i.e., either dithiochrome or insulin-dithiochrome adduct) given will depend on various factors, including the disease being treated, dithiochrome and to insulin-dithiochrome adduct may be administered to patients as follows.

For the treatment of conditions associated with elevated blood glucose or suboptimal glucose kinetics, including type II diabetes, insulin resistant diabetes, gestational diabetes, stress induced diabetes, obesity, and hyperlipidemia, dithiochrome may be administered to a human using a daily dosage of 0.1 microgram to 1 gram, preferably 1 to 200 micrograms, most preferably 10 to 50 micrograms.

The insulin-dithiochrome adduct may be injected in a manner similar to that used in conventional insulin therapy as a therapy for type I (juvenile or insulin-dependent) diabetes. The insulin-dithiochrome adduct may thus be used at a daily dosage of about 1 to $10^3$ units of insulin, preferably to 4 to $10^2$ units of insulin.

However it should be appreciated that it may be appropriate under certain circumstances to give daily dosages of either of these two materials either below or above these levels.

Other features of this invention will become apparent in the course of the following description of exemplary embodiments which are given for illustration of the invention and are not intended to be limiting thereof.

EXAMPLES

Purification of DTC

Distilled H$_2$O (200 ml) was added to 10.66 grams of Kal Brewer's Yeast Flakes. The mixture was stirred for 10 minutes. 200 ml of n-butanol was then added and the mixture was stirred for 230 minutes. The total stirring time was 240 minutes (4 hours). During this time the mixture turned to a pale yellow color.

The mixture was then placed in a separatory funnel at $4°$ C. overnight. The following day the mixture in the separatory funnel was too cloudy to distinguish a phase separation. Consequently the mixture was centrifuged at 10,000 RPM for 30 minutes at $4°$ C. The precipitate, which was eggshell white in color and looked like yeast, was discarded.

After centrifugation the two phases were apparent. The n-butanol phase on the top (d=0.809 g/ml) was a clear bright yellow color. The top phase was aspirated off the water extract phase and discarded. The bottom water extract phase (150 ml) was slightly cloudy and yellow in color.

The water extract phase was then lyophilized at −70° C. and 10 torr for 30 hours. The lyophilized powder was pale yellow in color. The sample was stored at −20° C.

Purification of DTC Using Insulin-Actigel Chromatography

A 200 mg sample of the lyophilized water extract was then dissolved in 5 ml of 25 mM $K_3PO_4$ buffer at pH 7.4 (buffer A). This was then incubated with 2 ml of Insulin-Actigel resin for 24 hours at 4° C. After incubation the Insulin-Actigel was poured into a 2 ml column (1 cm diameter) and washed with buffer A until a baseline was achieved (monitoring wavelength was 280 nm).

Figure 1:
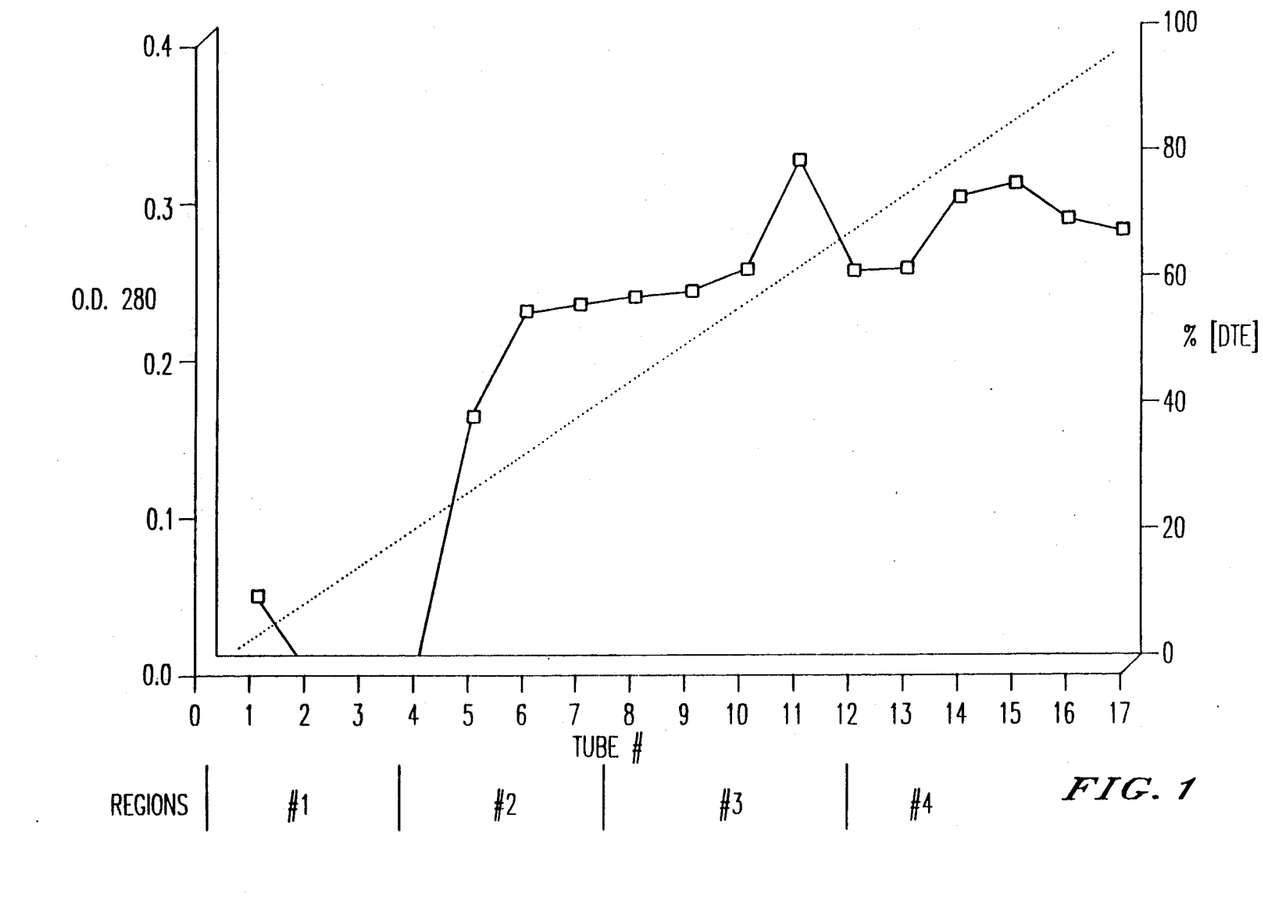
FIG. 1 illustrates the chromatogram obtained by eluting an Insulin-Actigel resin, having bound thereto dithiochrome, with a gradient of dithioerythrytol to cause the release of dithiochrome.

A dithioerythrytol (DTE) linear gradient 0–100% in 32 ml was applied to the FPLC column. FIG. 1 is a chromatogram of the gradient elution (100%–25 mM DTE). Four major "peaks" were eluted. The peaks were labeled "I" for insulin and in numerical order corresponding to their elution from the column. Peak I#1 was not pursued any further due to no U.V. absorbance at 280 nm. Peaks I#2, I#3, and I#4 were run on a 5 ml DEAE-Hiflow column using a NaCl linear gradient 0–1 M in 17 ml total elution volume. The samples were applied to the column at 0.3 ml/min. The DEAE work followed the paper of Votava (1975) except $O.D._{280}$ was monitored, and not $Cr^{3+}$.

Peak I#2 gave 4 peaks on DEAE. Peaks I#2 DEAE#1 and Peak I#2 DEAE#2 were the flow through and 0.5 M L- NaCl peaks. Peaks I#2 DEAE#3 and I#2 DEAE#4 were further characterized as discussed below. Peaks I#3 and I#4 gave only the flow through and 0.5 M NaCl peaks when run on DEAE.

Figure 2:
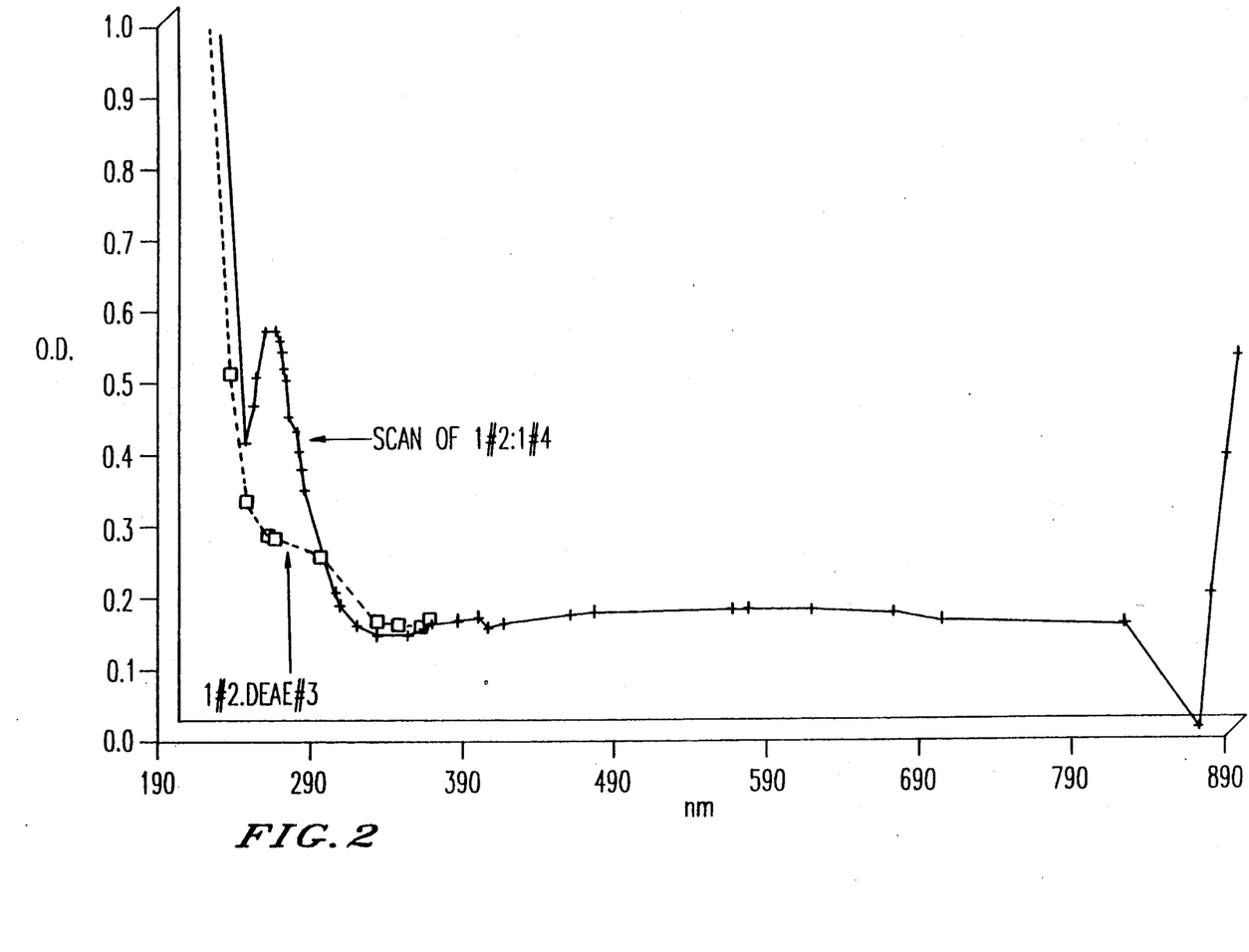
FIG. 2 is a UV-VIS spectru scan of region 2 obtained from the elution of the insulin column set out in FIG. 1, subjected to DEAE (cation-exchange) chromatography, regions 3 and 4, tested for the UV nicotinic acid peak.
Figure 3A:
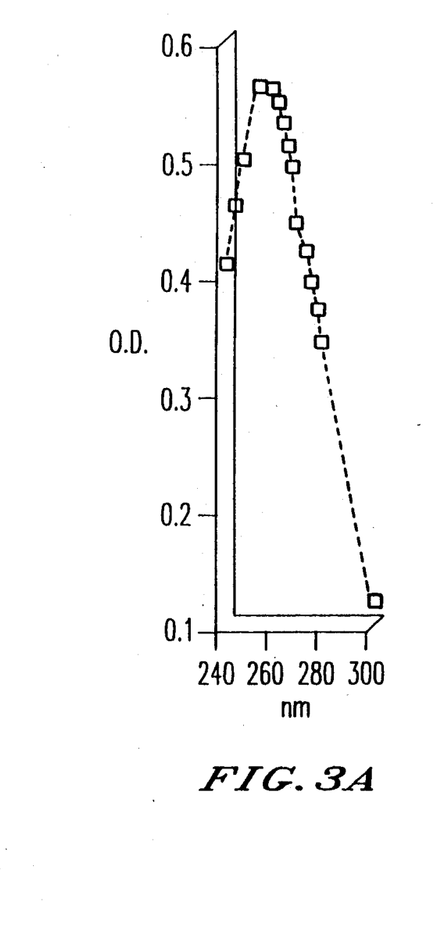
FIGS. 3A, 3B are a UV-scan comparing the scan of dithiochrome to the known UV-scan of GTF, synthetic GTF, and nicotinic acid.
Figure 3B:
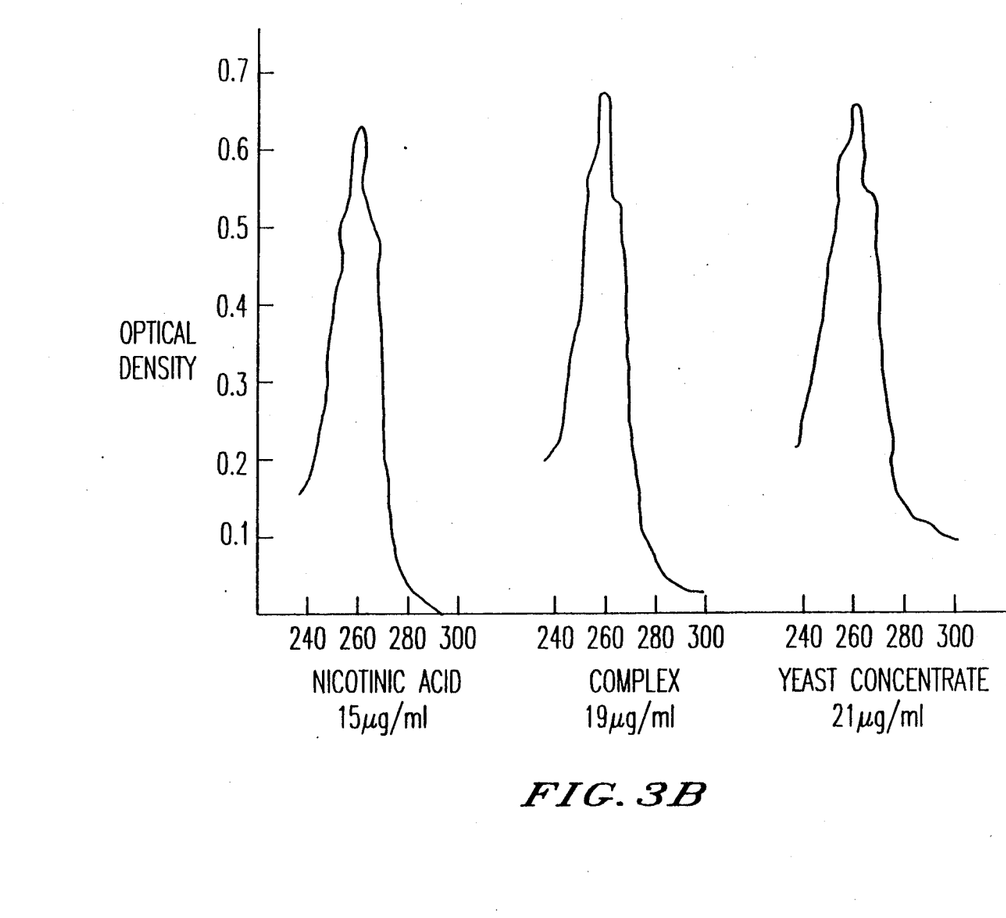

U.V. scans were run on I#2 DEAE#3 and I#2 DEAE#4 and the spectra appears in FIG. 2. The U.V. scan of I#2 DEAE#4 shows a peak at ∼260 nm—characteristic of nicotinic acid. To further illustrate this point a close-up of the U.V. spectrum of I#2 DEAE#4 is compared to known U.V. spectra of nicotinic acid, synthetic GTF and natural GTF in FIG. 3. Toepfer et al (1977).

Purification of DTC Using Actigel-T Chromatography

The cost of a 100 mL insulin column for scale up, that may be used only once, is undesirably high for the yields obtained with insulin. Dithiochrome apparently forms a disulfide bond with insulin so the inventors investigated the possibility that it may form a disulfide bond with Actigel T.

A 200 μl Actigel T resin was incubated with 2 mL of 0.1 M Tris, 0.1M NaCl and 5mM EDTA buffer at pH=8.0 and 10 mg of 1#2:DEAE#4 for 24 hrs. The solution had an initial $OD_{280}$ of 1.347 and $OD_{320}$ 0.105. The mixture was then filtered and found to have an $OD_{280}$ 1.194 and $OD_{320}$ 0.275 in the supernatant.

When Actigel T forms a disulfide bond with another ligand it releases an ylide that absorbs at 320nm. The results suggests that the isolated material has a titratable thiol group(s).

Knowing that Actigel T has a highly reactive disulfide, it will form a disulfide faster than insulin. The lyophilized water extract (600 mg) was added to 25 mL of Buffer A and 5 mM EDTA. Actigel T was packed into a 5 mL column and the sample extract was applied to the column at 0.1 mL/min. After the sample was loaded, the column was washed with buffer A and 6mM EDTA until a baseline was reached. A linear gradient (0–100% in 32 ml) using 10 mM dithiolerythrytol (DTE) (100%) was used (appendix 4). Both the Insulin-Actigel and the Actigel T chromatograms have similar peaks. Again the second eluted peak was applied to the 5 mL DEAE-Hiflow column and run as before. A large broad peak fell through the column and a single peak T#2 DEAE#2 was eluted by the salt gradient (appendix 5).

Figure 4:
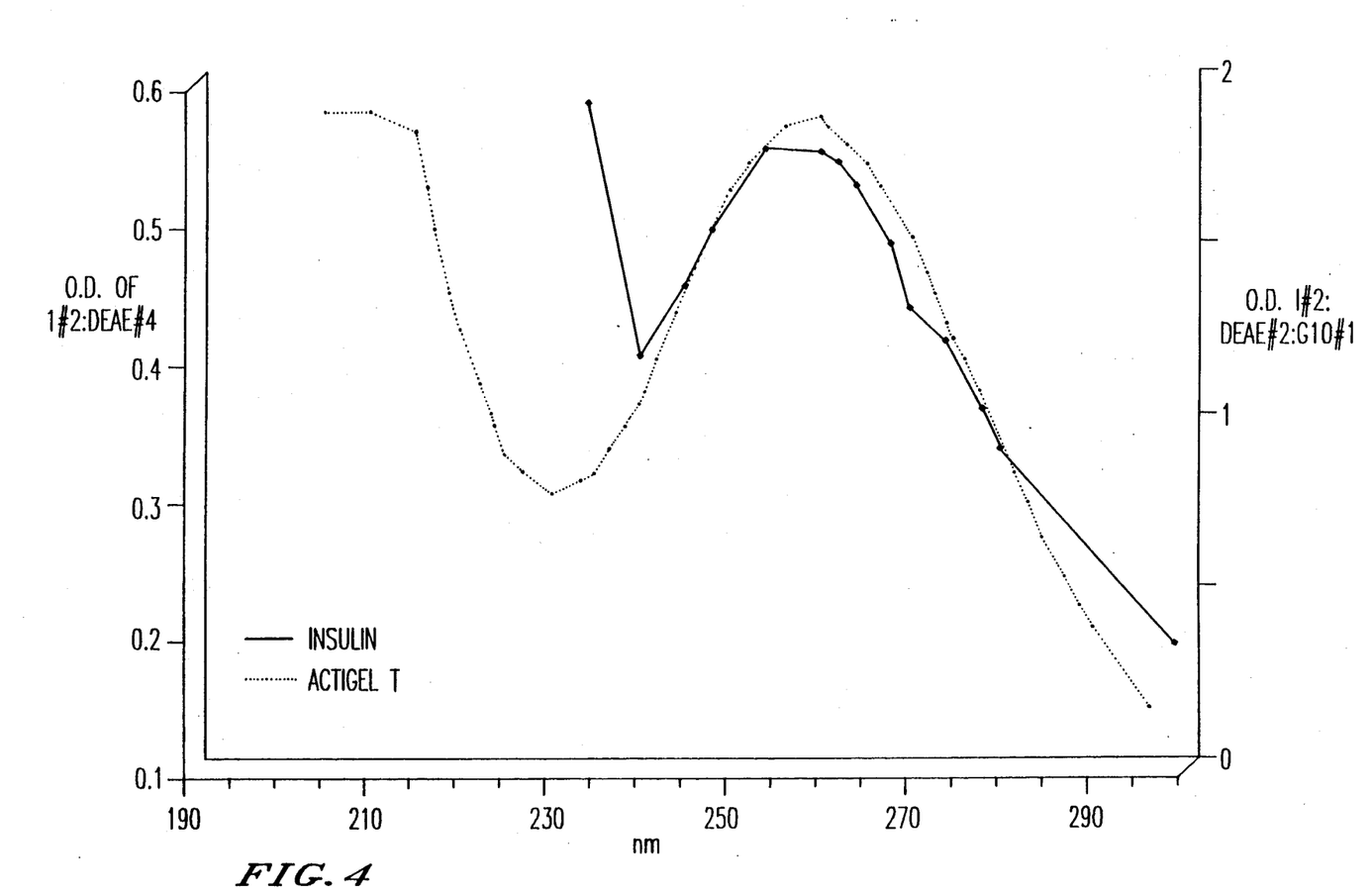
FIG. 4 is a comparison of the dithiochrome obtained using (i) an Insulin-Actigel column and (ii) an Actigel T column.

T#2 DEAE#2 was freeze-dried and weighed (800 mg). The material was then redissolved in d.i. water at 400 mg/mL and applied on a Sephadex G-10 column using d.i. water eluent (appendix 6). The gel filtration chromatograms of Actigel T and Insulin-Actigel purified materials look very similar. The collected elution volume was 8.2 mL; 1 mL of the fraction was used for UV scan and determining $E_i\%$ at 260 value. The material after freeze-drying weighed 5 mg. The calculated $E_1\%=52.0$ at 260 nm and pH 7.2. Comparisons of the isolated material by the Insulin-Actigel and Actigel T columns shows that the products are identical on ion exchange and gel filtration chromatography and by U.V. spectrum (FIG. 4).

| | Comparison of Actigel-T vs. Insulin-Actigel | | | | | |
|---|---|---|---|---|---|---|
| | Process Time | Binding Capacity | Resin Cost ml/day | Sanitization | Purity | Yield of % GTF in dried yeast extract |
| Actigel T | 5 mg/38 hrs | 40–50 μmol/ml | $0.01 | yes | higher | .83% |
| Insulin Actigel | .3 mg/85 hrs | 1.6 μmol/ml | $39.60 | no | lower | .3% |

Qualitative Test

Figure 5:
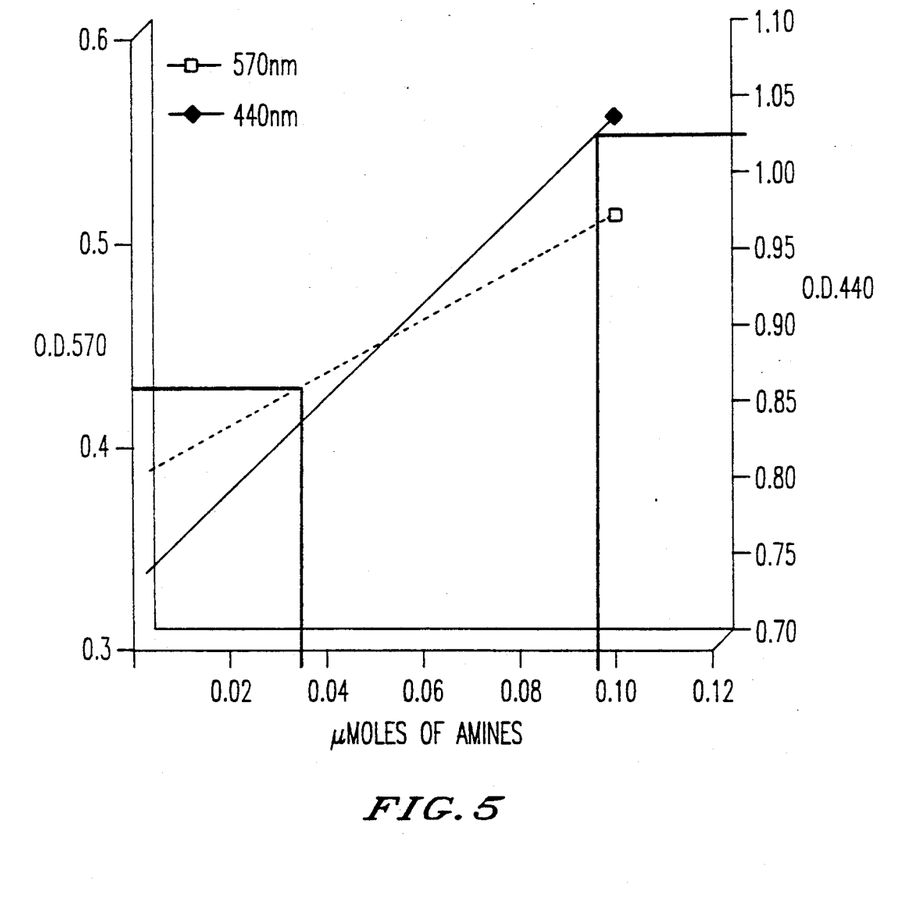
FIG. 5 plots the results obtained for a Ninhydrin test performed on dithiochrome.
Figure 6:
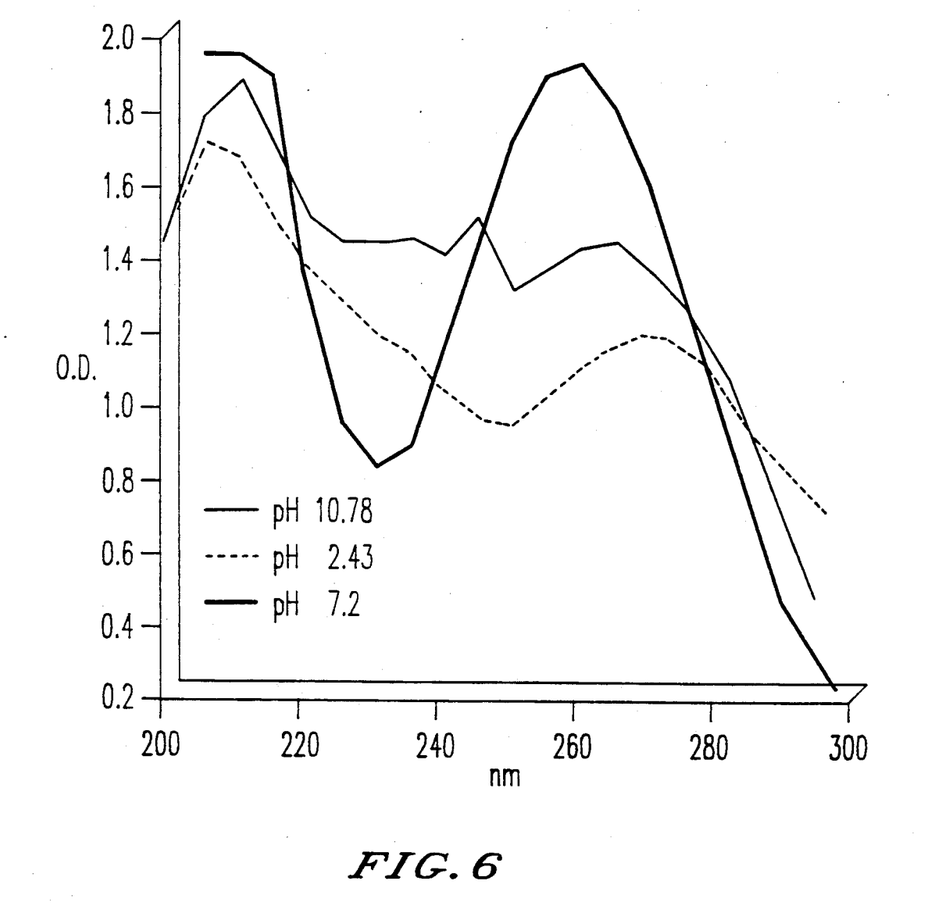
FIG. 6 shows the effect of pH on the UV absorbance of DTC.

The ninhydrin test for the isolated material came out positive for primary and secondary amines. The results are plotted in FIG. 5. These data suggest that the isolated material may contain amino acid residue(s).

Biological Activity (1) Cellular Assays of Insulin Action

Dithiochrome increases activity in insulin activity assays. The first attempt to perform the insulin activity assay was unsuccessful because the sample had been inactivated by lyophilization.

Figure 7:
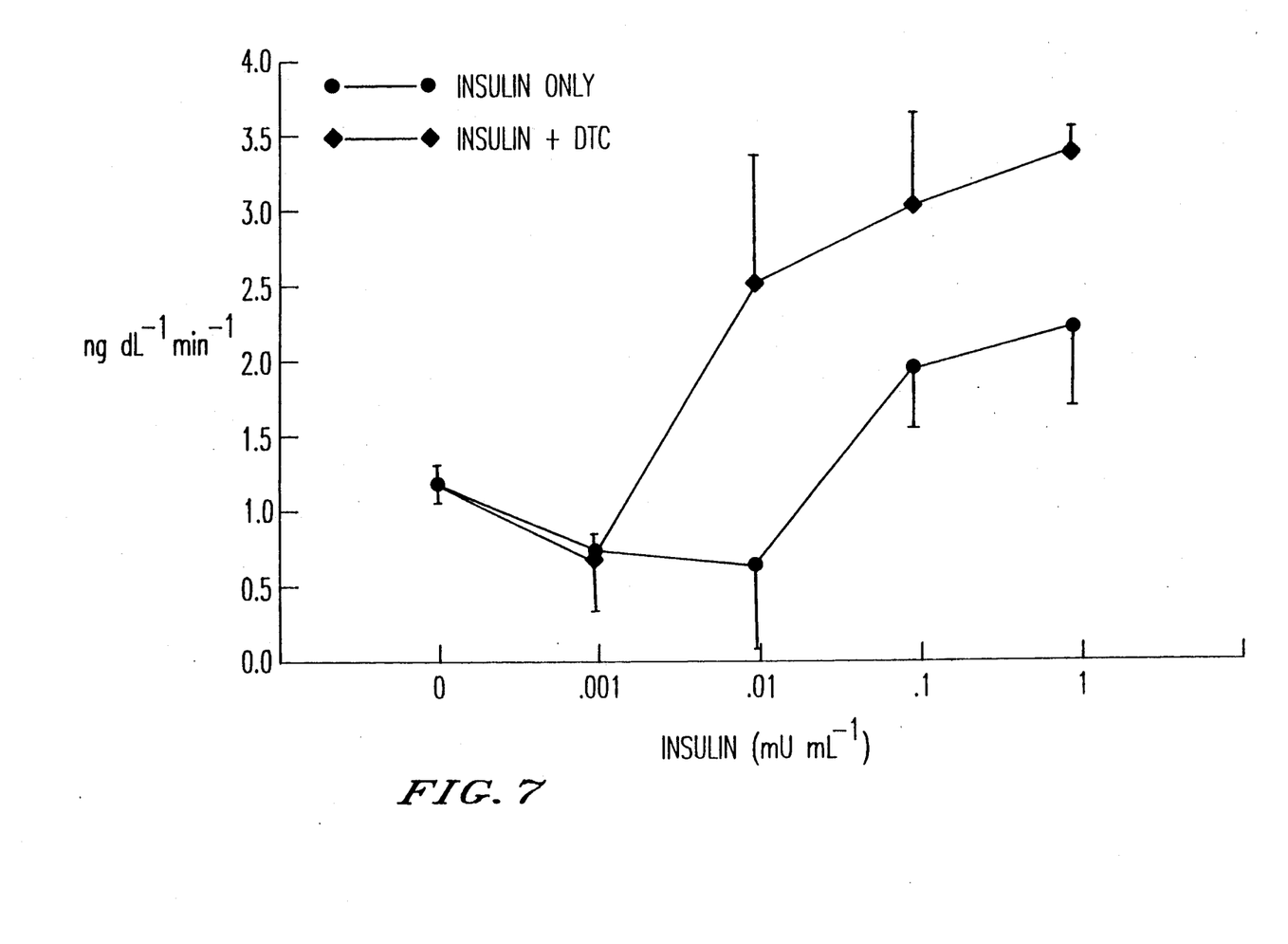
FIG. 7 provides data obtained from cellular assays of insulin action, showing DTC's activity in the treatment of diabetes.

Later attempts proved successful. FIG. 7 provides the data from a run of an assay designed to show whether dithiochrome increases the rate that adipocytes take up glucose. In this assay a human adipocyte cell line (American Type Culture Cell Line CCL 92.1) was grown to a monolayer, serum-free medium was added along with insulin and DTC, and the concentration of glucose was measured at 15-minute intervals for 90 minutes. The rate of glucose uptake was calculated.

In FIG. 7 the lower curve shows the classic sigmoid dependence of glucose uptake on insulin concentration (in the absence of dithiochrome). The line is the glucose uptake of control cells, i.e., insulin-independent glucose uptake. At a concentration of 0.001 mU insulin with or without dithiochrome the uptake is unchanged. At a concentration of 0.01 mU insulin, insulin alone causes no increase of glucose uptake. Addition of dithiochrome causes an increase to over three times control levels. This increase of insulin simulated uptake of glucose by dithiochrome continues at all higher insulin concentrations.

(2) Animal Models of Type II Diabetes

Dithiochrome is active in the treatment of insulin resistance disease in animal models.

The first test on diabetic animals, a bioassay, was performed on fatty Zucker rats developed at the University of Indiana.[1] The protocol was to use a sample of stabilized dithiochrome with a control solution with equal O.D. nicotinic acid with same stabilization buffer. Blood sugars were measured at various intervals. (1) Greenhouse, D. D., Michaelis, O. E., Peterson, R. G., "The Development of Fatty and Corpulent Rate Strains," New Models of Genetically Obsese Rats for Studies in Diabetes, Heart Disease, and Complications of Obesity, Hansel, C. T. and Michaelis, O. E., Eds., NIH, Division of Research Services, Veterinary Resources Branch (1988).

Figure 8:
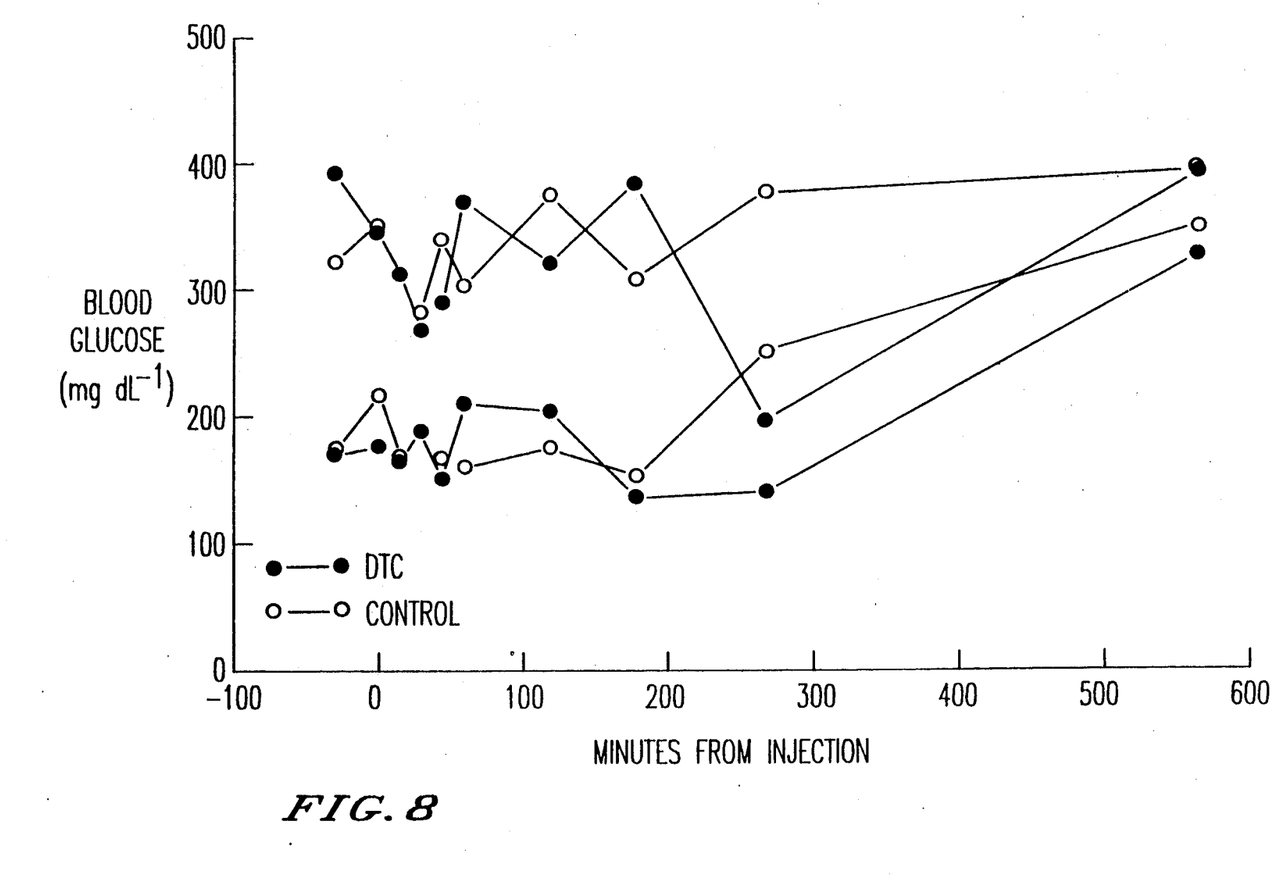
FIGS. 8, 9 and 10 show the effect of DTC injected in diabetic rats.
Figure 9:
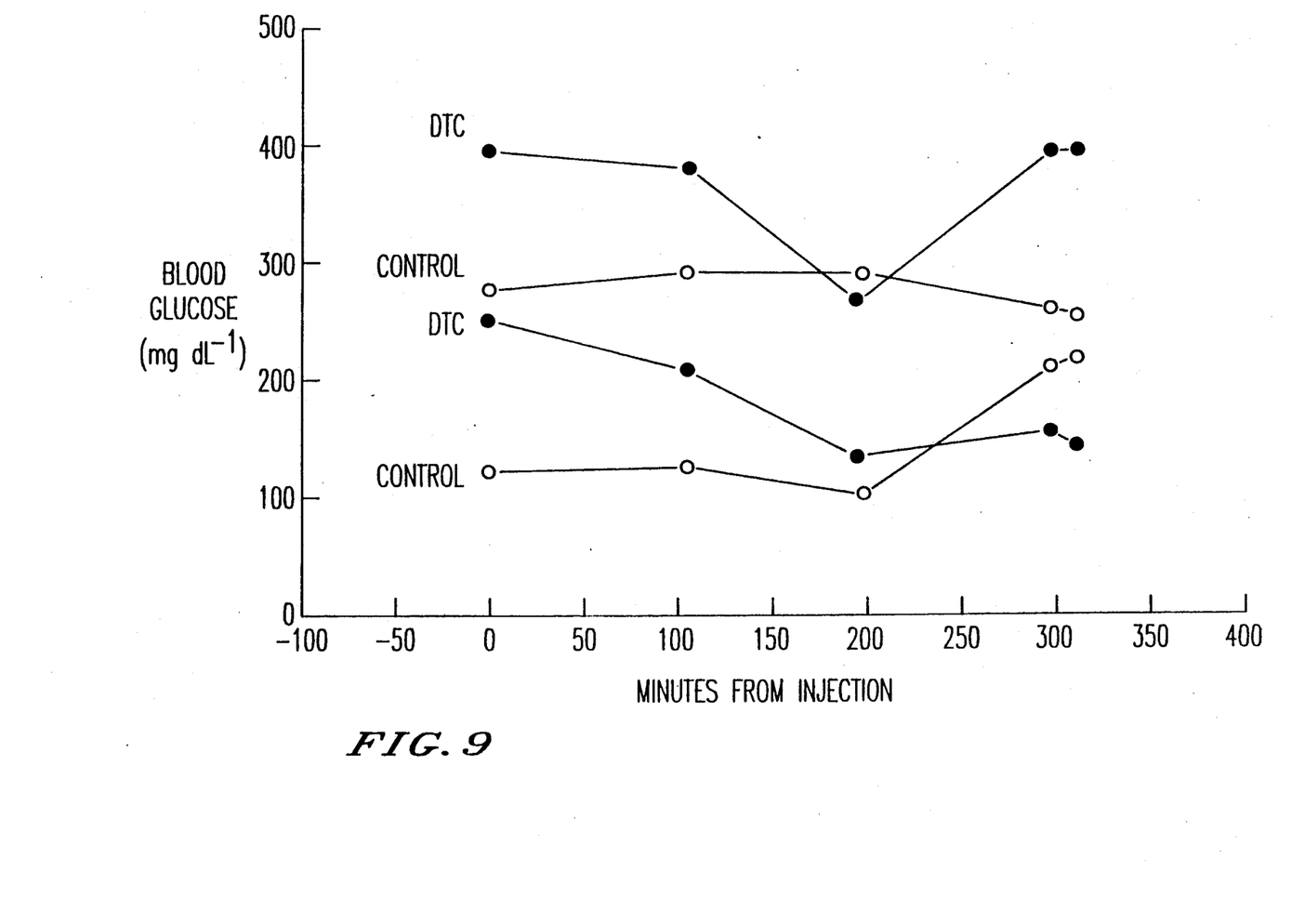
Figure 10:
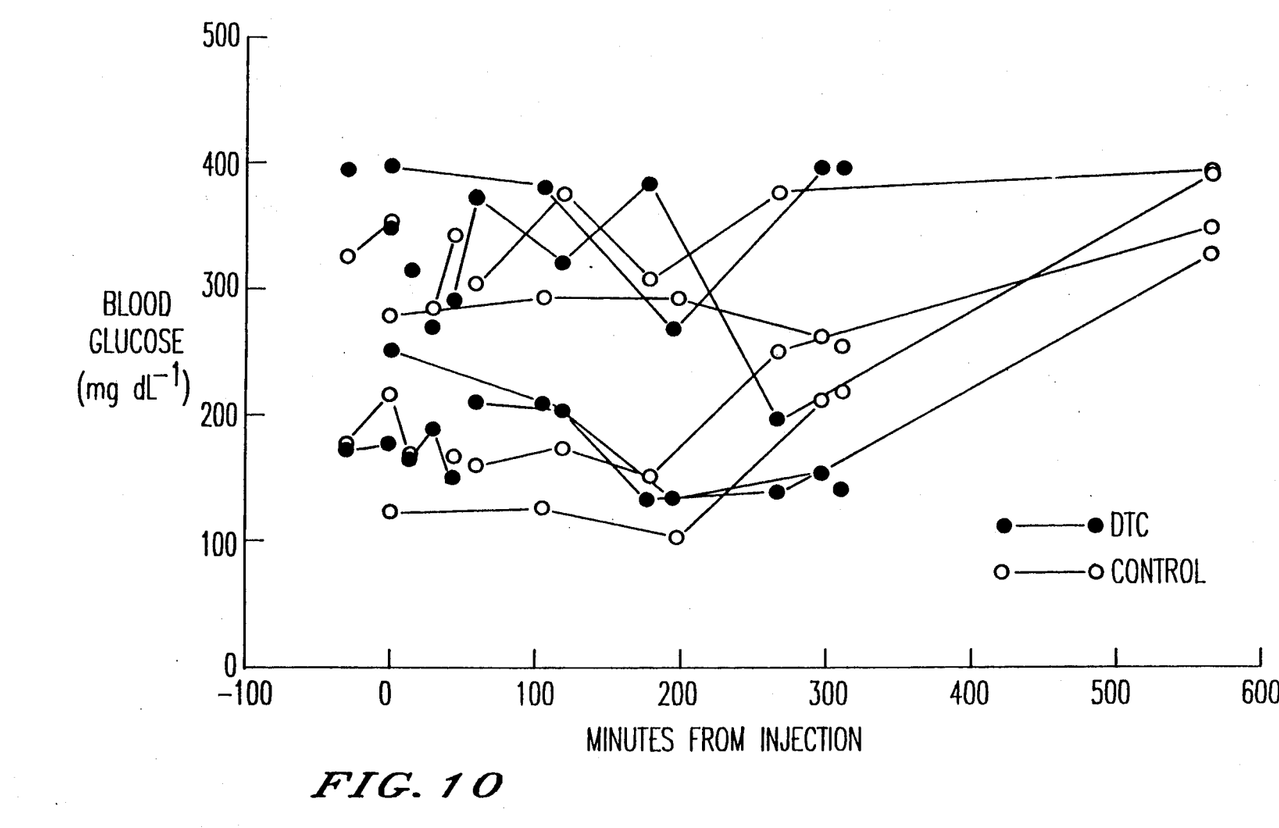

The graphs provided in FIGS. 8, 9 and 10 show the results obtained. The first graph (FIG. 8) shows the first experiments, the second graph (FIG. 9) shows the second experiments, and the third graph (FIG. 10) combines them on a single time axis. It was observed that the four controls had stable or rising blood sugar. The treated animals all showed a reduction in blood sugar from three to four hours post injection.

Obviously, numerous modifications and variations of the present invention are possible in light of the above teachings. It is therefore to be understood that within the scope of the appended claims, the invention may be practiced otherwise than as specifically described herein.

I claim:

1. A process for obtaining a material possessing glucose tolerance factor activity, comprising:
   (i) contacting a eukaryotic cell mass with a mixture of water and an alcohol to form a water phase and an alcohol phase;
   (ii) separating the alcohol phase from the water phase and isolating a water phase extract; and
   (iii) subjecting said water phase extract to gel exclusion chromatography, eluting all material having a molecular weight of approximately 720 to 1120 to obtain a material possessing glucose tolerance factor activity and capable of binding with insulin.

2. The process of claim 1, comprising eluting all material having a molecular weight of approximately 820 to approximately 1020.

3. A process for obtaining a material possessing glucose tolerance factor activity, comprising:
   (i) contacting a eukaryotic cell mass with a mixture of water and an alcohol to form a water phase and an alcohol phase;
   (ii) separating the alcohol phase from the water phase and isolating a water phase extract;
   (iii) freeze drying said water phase extract; and
   (iv) subjecting said freeze dried water phase extract to gel exclusion chromatography, eluting all material having a molecular weight of approximately 720 to 1120 to obtain a material possessing glucose tolerance factor activity and capable of binding with insulin.

* * * * *